United States Patent [19]
Kaneko

[11] Patent Number: 5,627,613
[45] Date of Patent: May 6, 1997

[54] OPHTHALMOLOGICAL ILLUMINATION DEVICE FOR OBSERVING AN EXAMINED EYE AND METHOD

[75] Inventor: Masanobu Kaneko, Yokohama, Japan

[73] Assignee: Nikon Corporation, Tokyo, Japan

[21] Appl. No.: 555,013

[22] Filed: Nov. 13, 1995

[30] Foreign Application Priority Data

Dec. 14, 1994 [JP] Japan ..................... 6-332993

[51] Int. Cl.⁶ .................................................. A61B 3/10
[52] U.S. Cl. .................................. 351/221; 351/205
[58] Field of Search ............................... 351/221, 211, 351/205, 220, 216, 214, 206

[56] References Cited

U.S. PATENT DOCUMENTS

| | | |
|---|---|---|
| 4,779,968 | 10/1988 | Sander . |
| 4,838,679 | 6/1989 | Bille ........................ 351/206 |
| 5,126,877 | 6/1992 | Biber . |
| 5,132,837 | 7/1992 | Kitajima . |

FOREIGN PATENT DOCUMENTS

| | | |
|---|---|---|
| 63-206221 | 8/1988 | Japan . |
| 63-206222 | 8/1988 | Japan . |
| 3-185415 | 8/1991 | Japan . |

*Primary Examiner*—Hung X. Dang
*Attorney, Agent, or Firm*—Oliff & Berridge

[57] ABSTRACT

The invention provides an ophthalmological illumination device which produces a plurality of illumination types using a single light source. The device illuminates the examined eye without causing damage to the maculalutea of the retina. The device illuminates the examined eye through an object lens and includes a light source means for supplying illumination light and a light separating means for separating the illumination light. The light separating means separates the light into a first illumination light which is incident on the object lens in a direction parallel with the optical axis of the object lens and a second illumination light. A movable inclining means causes the second illumination light to be incident on the object lens in a direction parallel with the optical axis. The angle of the second illumination light incident on the examined eye changes relative to the optical axis in accordance with the movement of the movable inclining means.

23 Claims, 5 Drawing Sheets

OPHTHALMOLOGICAL ILLUMINATION DEVICE FOR OBSERVING AN EXAMINED EYE AND METHOD

BACKGROUND OF THE INVENTION

1. Field of the Invention

The invention relates to an ophthalmological illuminating device and method, in particular it relates to an illuminating device of a surgical microscope for observing an examined eye.

2. Description of Related Art

Surgical microscope illumination devices provide coaxial illumination methods and oblique illumination methods. In the coaxial illumination method, the illumination optical axis and the observation optical axis of the microscope coincide so that the illumination light is not blocked by the edges of the illuminated viewing area. In the oblique illumination method, a large angle between the illumination optical axis and the observation optical axis of the microscope enables three-dimensional observation based on shadows generated by the illumination light.

The coaxial illumination method allows the illumination light to reach deeply in the viewing areas. The depth depends on the extent that the illumination optical axis coincides with the observation optical axis. However, damage to the macula lutea of the retina may occur by direct illumination.

In the coaxial illumination method, an illumination angle between the illumination optical axis and the observation optical axis of the microscope is changed by advancing or withdrawing a prism along the illumination light path. The illumination angle is also changed by moving the reflective mirror on the illumination optical axis.

The oblique illumination method is used when the coincidence of the illumination optical axis and the observation optical axis is not necessary. In general, the oblique illumination method is driven by a different power source than that of the coaxial illumination method. Thus, both an oblique illumination system and a coaxial illumination system are required for a surgical microscope. Accordingly, the size and cost of the illumination device are large and reduction in the size and cost of the illumination device are desired.

In order to reduce the size and cost of the illumination device, a reflective mirror is provided in a conventional illuminating device. The reflective mirror is moved into the illumination light path for oblique illumination and the reflective mirror is withdrawn from the illumination light path for coaxial illumination.

In the coaxial illumination method, when the illumination angle is changed by moving a prism into and out of the illumination light path, only predetermined illumination angles can be obtained. Consequently, intense light shining on the macula lutea of the retina may be unavoidable.

A continuous change in the illumination angle is achieved, when the illumination angle is changed by a reflective mirror in the coaxial illumination method. However, because the illumination light always has a fixed light quantity, excessive light shines on the macula lutea of the retina when the illumination angle is small.

Furthermore, when the reflective mirror is used to change between oblique illumination and coaxial illumination, concurrent use of both the coaxial illumination and the oblique illumination is impossible. Consequently, when using coaxial illumination with a narrow illumination field radius, it is impossible to illuminate the wide portions surrounding the perimeter of the viewing area.

SUMMARY OF THE INVENTION

It is an object of the invention to provide an ophthalmological illumination device for obtaining a plurality of illumination types using a single light source, and illuminating the examined eye without causing damage to the macula lutea of the retina.

The invention provides an ophthalmological illumination device which illuminates the examined eye. The illumination device includes an optical system which produces a plurality of light beams. The plurality of light beams illuminating the examined eye at a plurality of angles relative to an optical axis of an object lens. A portion of the plurality of angles is changeable. The optical system allows observation of the examined eye by means of the object lens.

The illumination device comprises a light source means for supplying illumination light, a light separating means and a movable inclining means. The light separating means separates the illumination light into a first illumination light which is incident on the object lens in a direction parallel with the optical axis of the object lens, and a second illumination light. The movable inclining means causes the second illumination light to be incident on the object lens. The angle of the second illumination light optical axis incident on the examined eye changes relative to the observation optical axis in accordance with the movement of the movable inclining means.

In preferred embodiments of the invention, the light separating means is a semi-transparent (or half-silvered) mirror which separates the illumination light from the light source means into light that passes through the mirror and light that reflects from the mirror. The movable inclining means is a completely reflective mirror which moves in a direction of the light which has passed through the semi-transparent mirror.

Another preferred embodiment provides a semi-transparent mirror having a first surface and a second surface. The first and second surfaces oppose each other. The illumination light from the light source is incident on the first surface and a semi-transparent membrane is formed on the second surface. A reflective membrane is formed on a surface of a completely reflective mirror and reflects light which has passed through the semi-transparent mirror. The reflective mirror is capable of moving until the reflective membrane contacts the semi-transparent membrane.

In the invention, the illumination light from the light source means is separated into two sections by a semi-transparent mirror. One section of the illumination light provides coaxial illumination of the examined eye at a predetermined angle of illumination by means of an object lens. The other section of the illumination light provides coaxial illumination of the examined eye at variable angles of illumination by directing the illumination light by inclining a movable completely reflective mirror guiding the illumination light through the object lens.

The ratio between the amount of light in one section of the illumination light and the amount of light in the other section of the illumination light can be adjusted by appropriately setting the reflectivity and the transmissivity of the semi-transparent mirror. In addition, as described above, the angle of illumination of one section of the illumination light is fixed, but the angle of illumination of the other section of the illumination light is variable.

Various coaxial illumination types are possible by combining the two sections of illumination light. By illuminating the examined eye using the combined sections of illumination light, damage to the macula lutea in the retina is avoided.

In addition, a portion of the illumination light from the light source means can be extracted and guided to the examined eye as oblique illumination light. Thus, both oblique illumination and coaxial illumination can be formed. Further, the angle of illumination is both variable and fixed providing needed illumination for various surgical procedures.

Another object of the invention is to provide a method for ophthalmological illumination. The method includes providing a light source which generates a light beam. A plurality of beam are produced from the light beam and the plurality of beam illuminates the examined eye at a plurality of angles relative to the optical axis of the object lens. A portion of the plurality of angles are changeable.

BRIEF DESCRIPTION OF THE DRAWINGS

The invention will be described in detail with reference to the following drawings, wherein.

DETAILED DESCRIPTION OF PREFERRED EMBODIMENTS

Preferred embodiments of the invention are described hereafter, with reference to the attached drawings.

Figure 1:
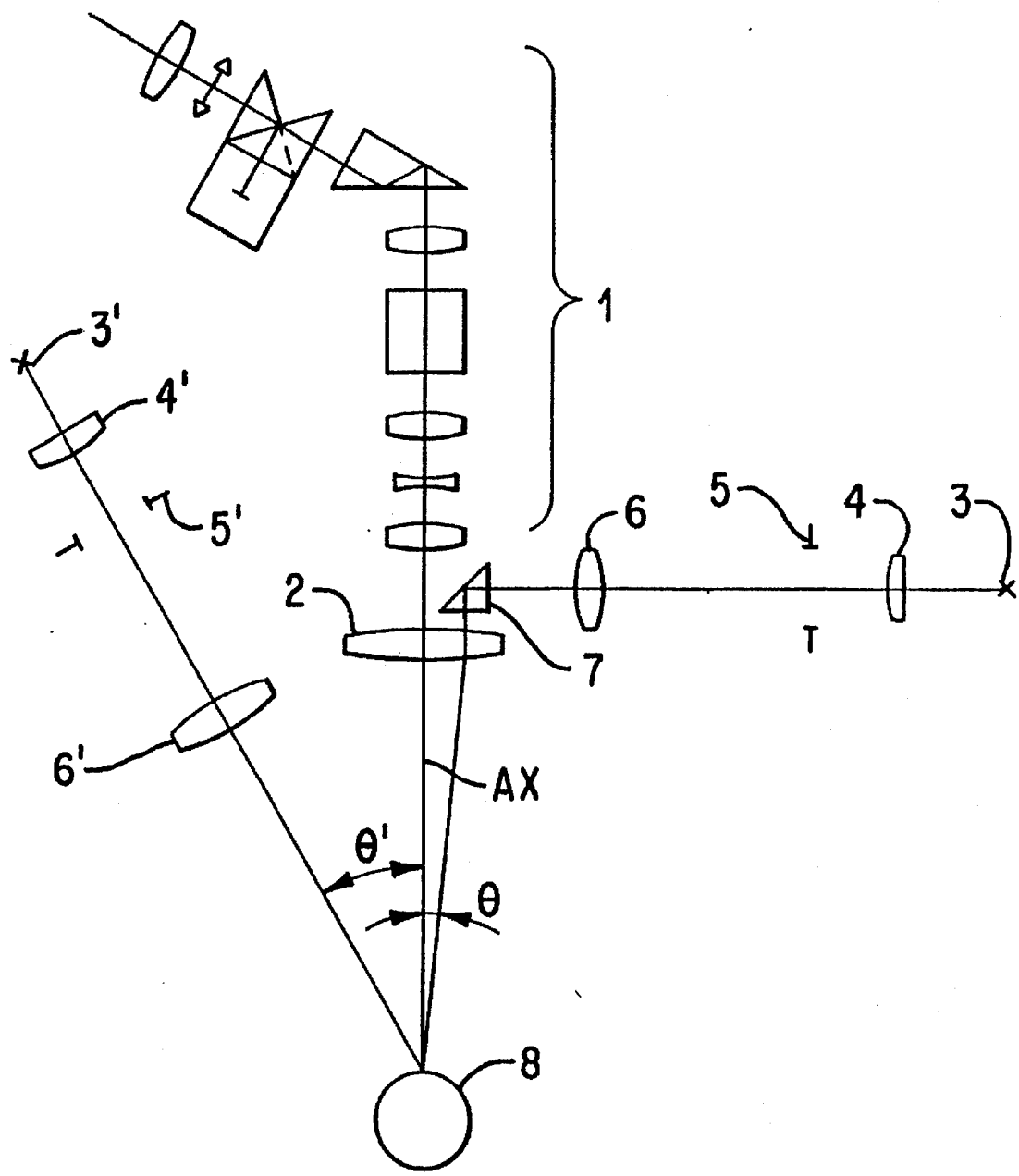
FIG. 1 is a schematic drawing of a surgical microscope.

FIG. 1 is a schematic drawing of a surgical microscope. A conventional coaxial optical illumination system and oblique optical illumination system are attached to the observation optical system 1 of the microscope.

An illumination light from the light source 3 is condensed by the condenser lens 4 and, after the illuminating field is restricted by an illuminating field diaphragm 5, the light is incident on the prism 7 via a relay lens 6. The light is inclined to be parallel with the optical axis AX of the observation optical system 1 by the prism 7. The light, passing through the object lens 2, illuminates the examined eye 8 at a small angle $\Gamma$ relative to the optical axis AX of the object lens 2. The object lens 2 is common with the observation optical system 1.

An oblique optical illumination system condenses a light generated by a light source 3' by a condenser lens 4'. After the illumination field is restricted by an illumination field diaphragm 5', the light is incident on relay lens 6'. The light which passes through the relay lens 6' illuminates the examined eye 8 with a large angle $\Gamma$ relative to the optical axis AX of the object lens 2.

Figure 2:
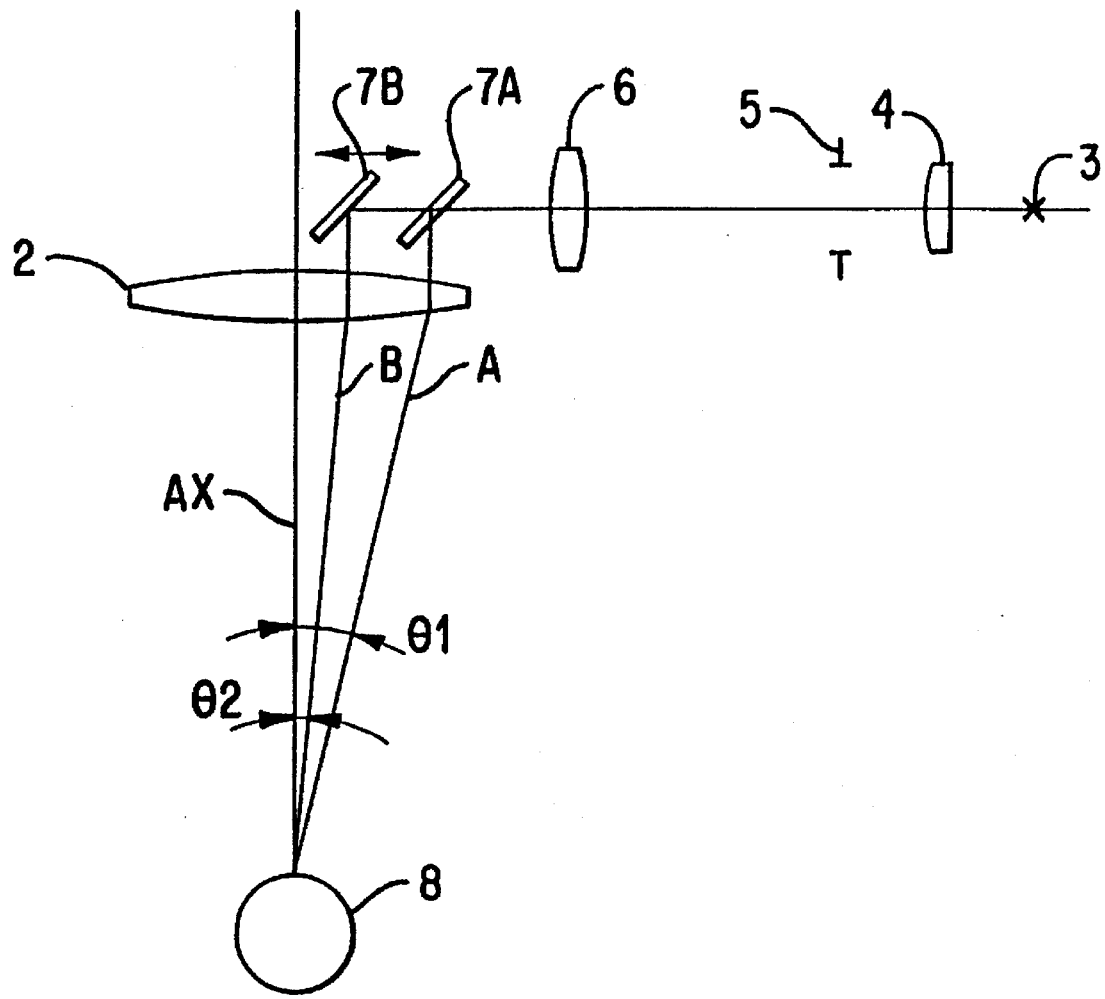
FIG. 2 is a schematic drawing of an ophthamological illumination device of a first embodiment of the invention.

FIG. 2 is a schematic drawing of an ophthalmological illumination device of a first embodiment of the invention. The object lens 2 corresponds to the object lens 2 of the observation optical system 1 of the surgical microscope of FIG. 1. The light generated by the light source 3 is condensed by a condenser lens 4. After the illumination field has been restricted by an illumination field diaphragm 5, the light is incident on a relay lens 6. The light, which passes through the relay lens 6, is divided by a semi-transparent mirror 7A into light which passes through and light which is reflected from the mirror 7A. The semi-transparent mirror has a transparent surface and a semi-transparent surface. The light from light source 3 is incident on the transparent surface.

The light which is reflected from the semi-transparent surface of the semi-transparent mirror 7A is parallel to the optical axis AX of the object lens 2. After passing through the optical lens 2, the reflected light from the semi-transparent mirror 7A illuminates the examined eye 8 along light path A with an angle 81 relative to the optical axis AX.

The light which passes through the semi-transparent surface of the semi-transparent mirror 7A is incident on the completely reflective mirror 7B. The light reflected from the reflective surface of the completely reflective mirror 7B is also parallel to the optical axis AX of the object lens 2. After passing through the object lens 2, the reflected light from the completely reflective mirror 7B illuminates the examined eye 8 along light path B with an angle $\mu 2$ relative to the optical axis AX.

As indicated by the arrows in FIG. 2, the completely reflective mirror 7B is movable along the illumination light optical axis containing the relay lens 6. Accordingly, when the location of surgery in the examined eye 8 cannot be adequately illuminated by the light along light path A, additional illumination is obtained by moving the completely reflective mirror 7B toward the optical axis AX to reduce the angle $\Gamma 2$. Thus, the ophthalmological microscope of the embodiment, using a single light source, simultaneously illuminate the examined eye with an illumination light having both a variable axial angle and an illumination light having a fixed axial angle.

Damage to the macula lutea in the retina of the examined eye 8 is avoided by appropriately setting the ratio between the transmissivity and the reflectivity of the semi-transparent mirror 7A which balances the light quantities in the variable axial angle illumination light and the fixed axial angle illumination light.

Figure 3:
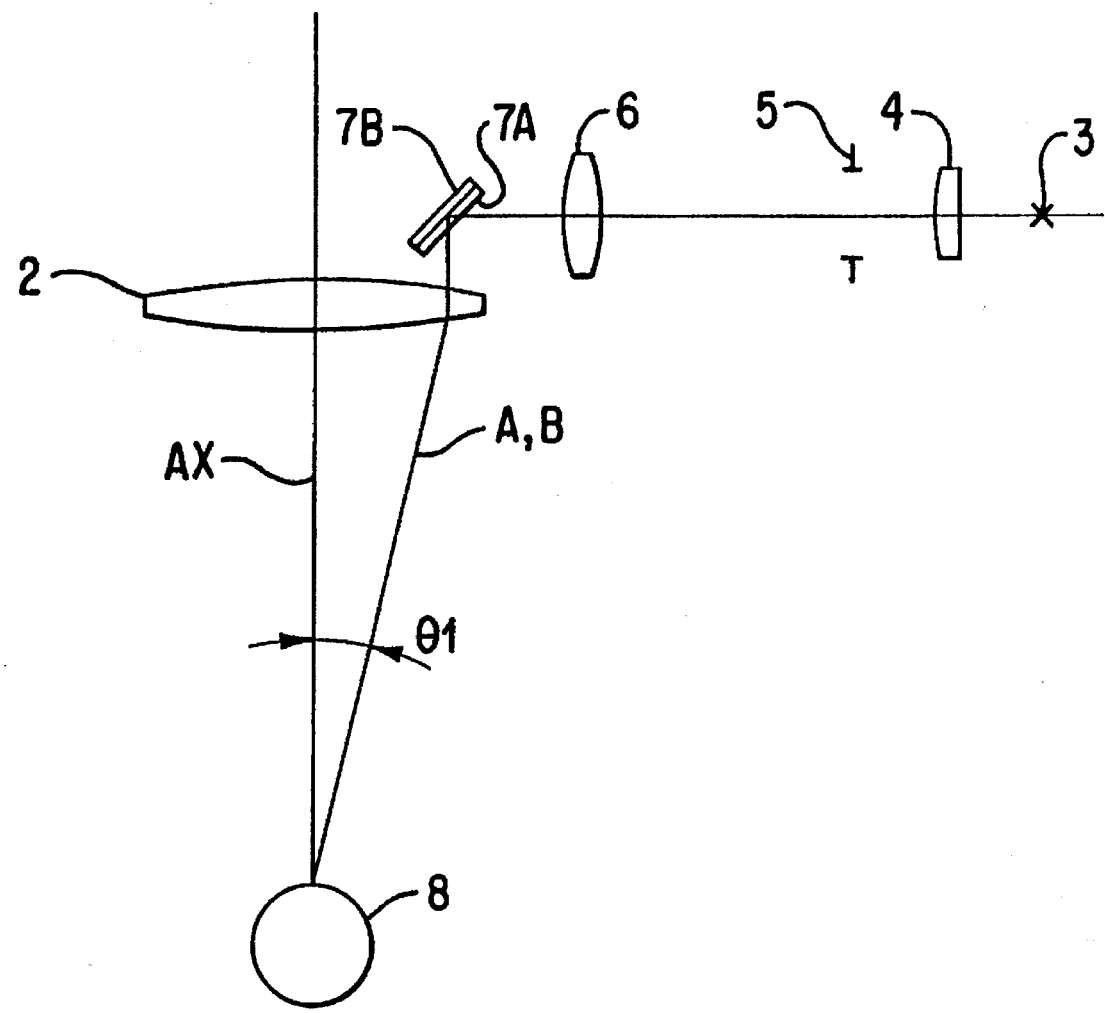
FIG. 3 is the device of FIG. 2 having a completely reflective mirror in contact with a semi-transparent mirror.

In addition, the same light quantity as provided by the conventional coaxial optical illumination system is obtained along light path A at an angle $\Gamma 1$ relative to the optical axis AX by moving the completely reflective mirror 7B to come in contact with the semi-transparent mirror 7A as shown in FIG. 3.

Figure 4:
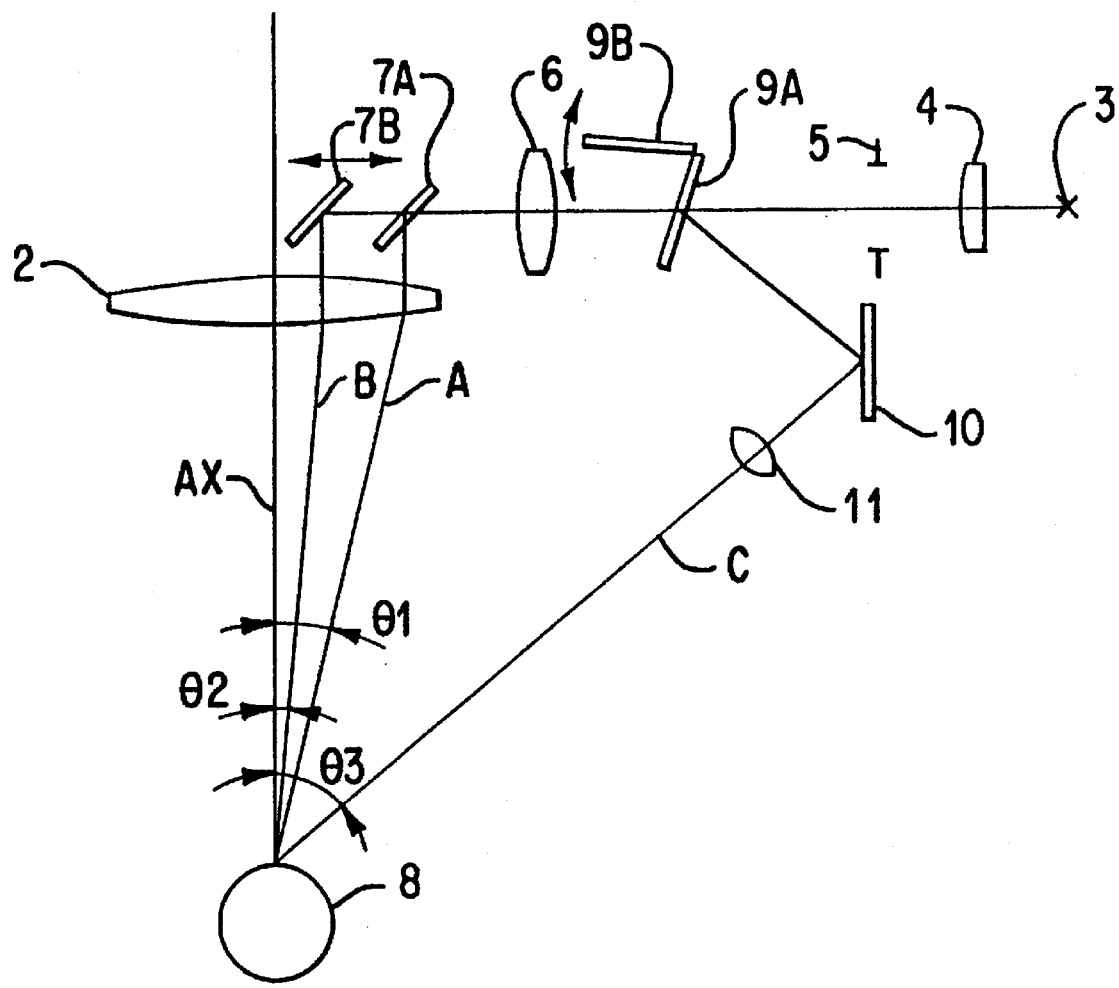
FIG. 4 is a schematic drawing of an ophthalmological illumination device of a second embodiment of the invention.

FIG. 4 is a schematic drawing of an ophthalmological illumination device of a second embodiment of the invention. The embodiment provides a semi-transparent mirror 9A between the illumination field diaphragm 5 and the relay lens 6. The semi-transparent mirror 9A has a transparent surface and a semi-transparent surface. The light from the light source 3 is incident on the transparent surface. The light generated by the light source 3 is condensed by the condenser lens 4, and after the illumination field is restricted by the illumination field diaphragm 5, the light is divided into a light which passes through and a light which is reflected by the semi-transparent mirror 9A.

The light which is reflected from the semi-transparent surface of the semi-transparent mirror 9A is guided to the completely reflective mirror 10. Light reflected from the completely reflective mirror 10 passes through a relay lens 11 and illuminates the examined eye 8 along light path C at a large angle $\Gamma 3$ relative to the optical axis AX of the object lens 2.

Light which passes through the semi-transparent mirror 9A is incident on the relay lens 6. The light passing through the relay lens 6 is divided into a light which passes through and a light which is reflected from the semi-transparent mirror 7A. The light which has been reflected from the semi-transparent surface of the semi-transparent mirror 7A is parallel to the optical axis AX of the object lens 2. After passing through the object lens 2, the light reflected from the semi-transparent mirror 7A illuminates the examined eye 8 along light path A at an angle Γ1 relative to the optical axis AX.

The light which passes through the semi-transparent surface of the semi-transparent mirror 7A is incident on the completely reflective mirror 7B. The light reflected from the reflective surface of the completely reflective mirror 7B is parallel to the optical axis AX of the object lens 2. After passing through the object lens 2, the light reflected from the completely reflective mirror 7B illuminates the examined eye 8 along light path B at an angle Γ2 relative to the optical axis.

As indicated by the arrows in the drawing, the completely reflective mirror 7B is movable along the illumination optical axis which contains the relay lens 6. Accordingly, the embodiment allows the illumination angle of light path B to be changed.

The ophthalmological illumination device of the invention, using a single light source forms oblique illumination and coaxial illumination having a variable illumination angle, and coaxial illumination having a fixed illumination angle. The light quantities of the variable and fixed angle coaxial illumination lights and the oblique light are balanced by setting an appropriate value for the ratio between the transmissivity and reflectivity of the semi-transparent mirror 9A. Thus, the invention obtains illumination that provides a wider range of surgical procedures.

Figure 5:
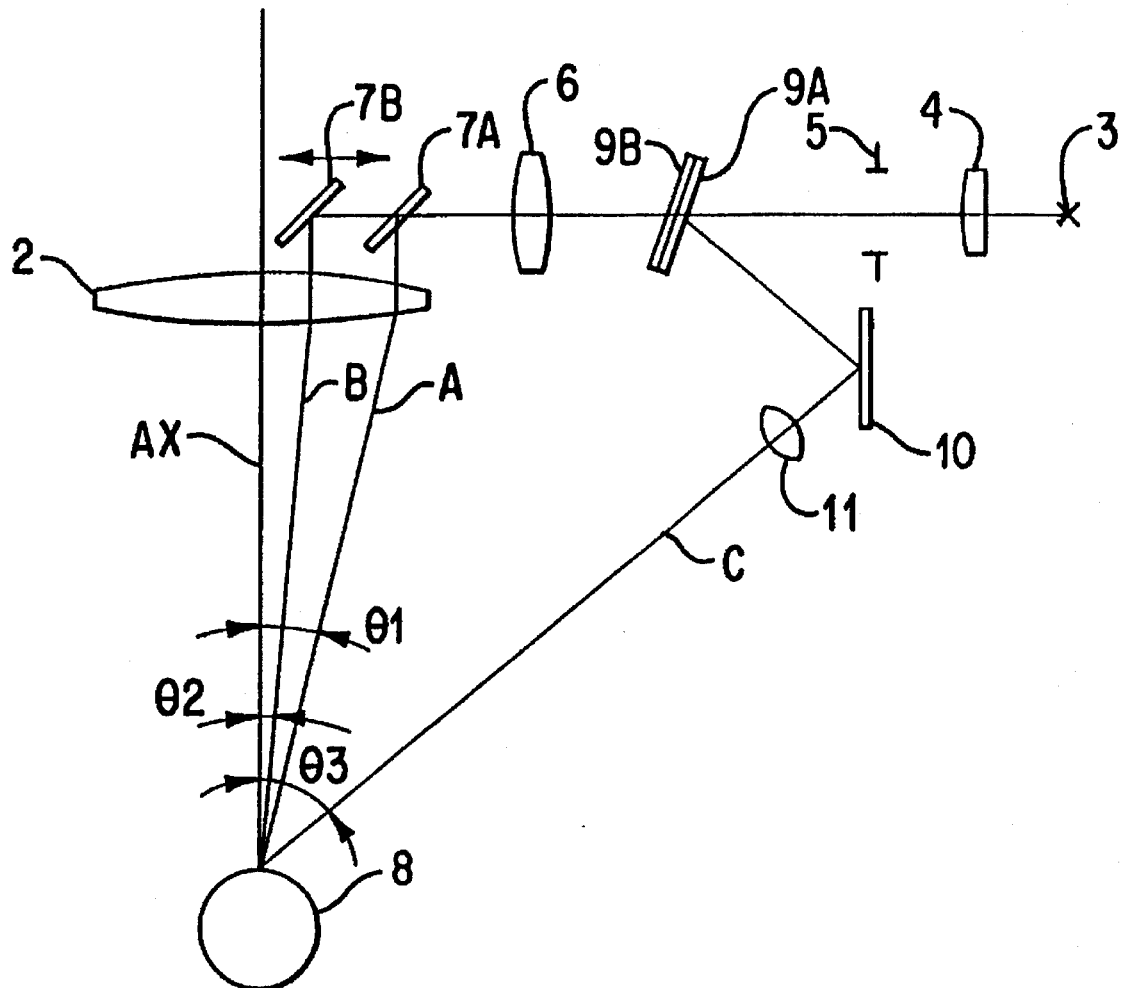
FIG. 5 is the device of FIG. 4 having a completely reflective mirror in contact with a semi-transparent mirror.

In addition, a completely reflective mirror 9B (surface mirror), can be moved into and withdraw from the illumination light path. In FIG. 5, the completely reflective mirror 9B contacts the semi-transparent mirror 9A. The completely reflective mirror 9B guides all the light from the light source 3 to illuminate the examined eye 8 along light path C of oblique illumination, thereby enabling bright oblique illumination.

The ophthalmological illumination device of the invention provides a variety of illuminations using a single light source, making it possible to illuminate a examined eye without causing damage to the macula lutea of the retina.

While this invention has been described in conjunction with specific embodiments thereof, it is evident that many alternatives, modification and variations will be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. An ophthalmological illumination device illuminating an examined eye, comprising:
    a light source generating a light beam; and
    an optical system including an object lens, the optical system receiving the light beam and producing a plurality of light beams, the plurality of light beams illuminating the examined eye at a plurality of angles relative to an optical axis of the object lens, a portion of the plurality of angles being changeable.

2. The ophthalmological illumination device of claim 1, wherein the plurality of light beams illuminate the examined eye with a plurality of light quantities of the plurality of light beams.

3. The ophthalmological illumination device of claim 2, wherein the optical system, further includes:
    a first light separator separating the light beam from the light source into a first light beam and a second light beam;
    the first light beam being parallel to the optical axis, when incident on the object lens; and
    a first light deflector that deflects the second light beam to be incident on the object lens in a direction parallel to the optical axis of the object lens, after passing through the object lens, the second light beam being incident on the examined eye so that the second light beam forms an angle with the optical axis of the object lens, the angle changing based on a movement of the first light deflector.

4. The ophthalmological illumination device of claim 3, wherein the first light separator is a semi-transparent mirror, the semi-transparent mirror separating the light beam of the light source into the first and second light beams, the first light beam reflecting from the semi-transparent mirror and the second light beam passing through the semi-transparent mirror.

5. The ophthalmological illumination device of claim 4, wherein the first light deflector is a completely reflective mirror, the completely reflective mirror being movable along an axis of the first light beam.

6. The ophthalmological illumination device of claim 5, wherein the semi-transparent mirror has a first surface and a second surface, the light beam from the light source being incident on the first surface, and a semi-transparent layer being formed on the second surface.

7. The ophthalmological illumination device of claim 6, wherein the semi-transparent layer is a half-silvered layer.

8. The ophthalmological illumination device of claim 6, wherein the plurality of light quantities of the plurality of light beams being balanced by setting a ratio of transmissivity and reflectivity of the semi-transparent mirror.

9. The ophthalmological illumination device of claim 6, wherein the completely reflective mirror has a completely reflective layer, the first light beam being incident on the completely reflective layer, the completely reflective layer contacting the semi-transparent layer of the semi-transparent mirror when the completely reflective mirror is moved to contact the semi-transparent mirror.

10. The ophthalmological illumination device of claim 3, further comprising a second light separator and a second light deflector, the second light separator separating the light beam from the light source into a third light beam and a fourth light beam, the third light beam being incident on the first light separator and fourth light beam being incident on the second light deflector, the second light deflector deflecting the fourth light beam to the examined eye at a predetermined angle relative to the optical axis of the object lens.

11. The ophthalmological illumination device of claim 10, wherein the second light deflector is a completely reflective mirror.

12. The ophthalmological illumination device of claim 10, wherein the second light separator is a semi-transparent mirror.

13. The ophthalmological illumination device of claim 12, wherein the semi-transparent mirror has a first surface and a second surface, the light beam from the light source being incident on the first surface, and a semi-transparent layer being formed on the second surface.

14. The ophthalmological illumination device of claim 13, wherein the semi-transparent layer is a half-silvered layer.

15. The ophthalmological illumination device of claim 13, wherein the plurality of light quantities of the plurality of light beams are balanced by setting a ratio of transmissivity and reflectivity of the semi-transparent mirror.

16. The ophthalmological illumination device of claim 13, further comprising a reflector, the reflector having a first position that reflects the third light beam into the same direction as the fourth light beam and a second position that does not reflect the third light beam.

17. The ophthalmological illumination device of claim 16, wherein the reflector comprises a reflective layer, the reflective layer contacting the semi-transparent layer when the reflector reflecting the third light beam.

18. A method for ophthalmological illumination of an examined eye, comprising:

providing a light source for generating a light beam; and producing a plurality of light beams from the light beam, the plurality of light beams illuminating the examined eye at a plurality of angles relative to an optical axis of an object lens, a portion of the plurality of angles being changeable.

19. The method of claim 18, wherein producing a plurality of light beams comprises:

separating the light beam into a first light beam and a second light beam;

directing the first light beam on the object lens in a direction parallel to the optical axis of the object lens; and directing the second light beam with a light deflector, the second light beam being deflected in a direction parallel to the optical axis of the object lens, after passing through the object lens, the second light beam forming an angle relative to the optical axis of the object lens, the angle changing based on a movement of the light deflector.

20. The method of claim 19, further comprising:

separating the light beam into a third light beam and a fourth light beam; and directing the fourth light beam on the examined eye at a predetermined angle.

21. The method of claim 20, wherein the third light beam are directed in the same direction as the fourth light beam.

22. An ophthalmological illumination device illuminating an examined eye, comprising:

light generating means for generating a light beam;

light separating means for separating the light beam into a plurality of light beams; and light deflecting means for deflecting a first portion of the plurality of light beams toward an object lens, the first light beam being parallel to an optical axis of the object lens, the first light beam passing through the object lens and being incident on the examined eye at angles relative to the optical axis of the object lens, the angles changing based on movements of the light deflecting means.

23. The ophthalmological illumination device of claim 22, wherein a second portion of the plurality of light beams is deflected to be incident on the examined eye at fixed angles relative to the optical axis of the object lens.

* * * * *